United States Patent [19]
Colomban et al.

[11] Patent Number: 6,099,883
[45] Date of Patent: Aug. 8, 2000

[54] ESSENTIALLY NON-DAIRY AQUEOUS FOOD COMPOSITION HAVING A CONSTANT BACTERIOLOGICAL QUALITY, AND METHOD FOR INHIBITING BACTERIAL GROWTH IN A FOOD COMPOSITION

[75] Inventors: François Colomban, Paris; Benoît Furhmann, Les Essarts le Roi; Xavier Modamio, Verrières les Buissons, all of France

[73] Assignee: Compagnie Gervais Danone, Levallois-Perret, France

[21] Appl. No.: 09/125,556

[22] PCT Filed: Feb. 27, 1997

[86] PCT No.: PCT/FR97/00350

§ 371 Date: Aug. 28, 1998

§ 102(e) Date: Aug. 28, 1998

[87] PCT Pub. No.: WO97/31547

PCT Pub. Date: Sep. 4, 1997

[30] Foreign Application Priority Data

Feb. 29, 1996 [FR] France ................... 96 02572

[51] Int. Cl.$^7$ .................................................. A23L 3/3571
[52] U.S. Cl. .................. 426/335; 426/532; 426/572; 426/593; 426/660
[58] Field of Search ............................ 426/61, 63, 330.1, 426/330.3, 335, 532, 568, 572, 579, 593, 605, 613, 614, 654, 659, 660

[56] References Cited

U.S. PATENT DOCUMENTS

| | | | |
|---|---|---|---|
| 4,587,130 | 5/1986 | Stauber | 426/564 |
| 5,266,338 | 11/1993 | Cascione et al. | 426/32 |
| 5,378,286 | 1/1995 | Chiou et al. | 127/36 |
| 5,543,325 | 8/1996 | Chatzopoulou et al. | 435/259 |

FOREIGN PATENT DOCUMENTS

| | | |
|---|---|---|
| 52 041 224 | of 1977 | Japan . |
| 90/04336 | 5/1990 | WIPO . |

OTHER PUBLICATIONS

Medrich, *Chocolate and the art of low–fat desserts*, Warner Books, Inc., pp. 145, 148, 1994.

*Primary Examiner*—Keith D. Hendricks
*Attorney, Agent, or Firm*—Finnegan, Henderson, Farabow, Garrett & Dunner, L.L.P.

[57] ABSTRACT

The present invention provides essentially non-dairy food compositions containing at least one monosaccharide in an amount sufficient to increase the osmotic pressure of the composition, and at least one bacteriocidal enzyme. The invention also provides methods of making such compositions. The food compositions preferably contain chocolate. The combination of at least one monosaccharide and at least one bacteriocidal enzyme inhibits increases in bacterial population numbers for at least 28 days.

31 Claims, 1 Drawing Sheet

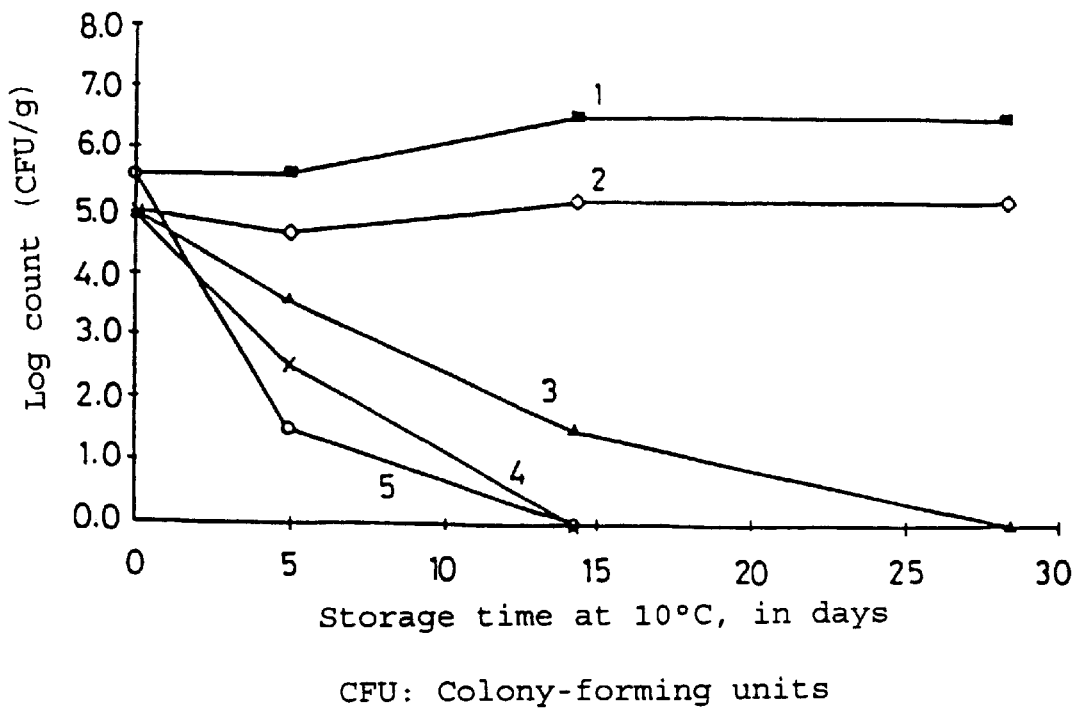
FIG_1
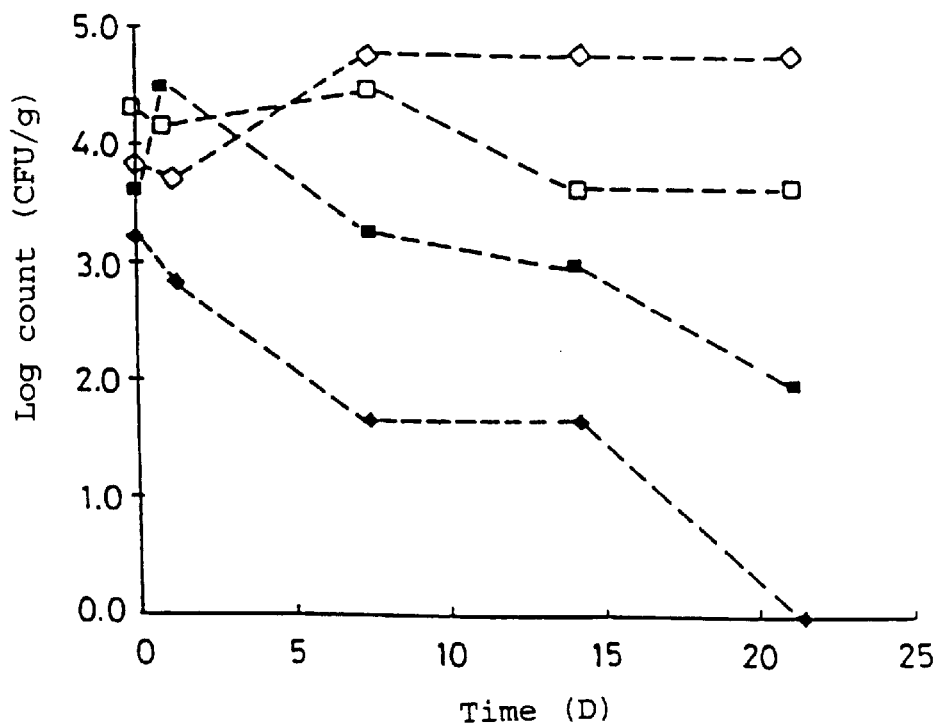
FIG_2

ESSENTIALLY NON-DAIRY AQUEOUS FOOD COMPOSITION HAVING A CONSTANT BACTERIOLOGICAL QUALITY, AND METHOD FOR INHIBITING BACTERIAL GROWTH IN A FOOD COMPOSITION

This application is a 371 of PCT/FR97/00350, filed Feb. 27, 1997.

BACKGROUND OF THE INVENTION

1. Field of the Invention

The present invention relates to an essentially non-dairy aqueous food composition which is of constant bacteriological quality over a suitable period.

The invention also relates to a method for inhibiting bacterial growth or for substantially reducing the bacterial population in a food or cosmetic composition.

The present invention relates more particularly to food compositions or products based on fresh produce which need to be stored at low temperature, for example in a refrigerator, for a suitable period, such as the amount of time required for the distribution of the product and delayed use of the products by the consumer.

2. Description of Related Art

During the manufacture of food compositions, in particular those based on fresh produce, it may be necessary to incorporate therein certain ingredients and foods (chocolate, egg yolk, various powders, cereals, spices, biscuits, dried fruit, dehydrated fruit, etc.) of nutritional, organoleptic or technological value, which can impair their marketing and hygiene qualities. For example, the addition of chocolate to the composition of dairy desserts can lead to microbial contamination of the finished product due in particular to the presence of sporulated bacteria in the chocolate.

The search for solutions capable of overcoming these drawbacks is of major interest for the use of these ingredients, in particular for the preparation of new products.

At the present time, the standard techniques of antimicrobial heat treatment are liable to modify the organoleptic, nutritional or technological qualities of the foods and ingredients treated. Furthermore, the type of microorganisms present, in particular sporulated bacteria, and the environment in which they are found, for example ingredients with a low water activity, or even with a high lipid or protein content, entail heat treatment conditions that are relatively incompatible with industrial realities.

In recent years, novel technological methods have been studied, such as very high pressures, ionization, infrared treatment, ultraviolet treatment, etc. However, these methods also find their limitation, the compromise between the antimicrobial efficacy and the maintenance of the organoleptic qualities not always being satisfactory.

As a general rule, fresh produce must retain its organoleptic qualities and its bacteriological characteristics for 28 days at 60° C. However, produce on the market can undergo temperature variations resulting in storage above 6° C. Consequently, it is preferable for the produce to also retain its stability for at least 3 hours of storage at 30° C. and, even more preferably for 28 days of storage at 10° C.

SUMMARY OF THE INVENTION

The object of the present invention is to propose new means and food compositions which achieve, at least partially, the following goals:

maintenance of the organoleptic, nutritional or technological value of the ingredient treated by the method, satisfactory reduction of the microbial flora, in particular of the pathogenic bacteria (*Bacillus cereus, Escherichia coli, Staphylococcus aureus, Salmonella enteritidis, Listeria monocytogenes*, etc.) taking into account the bacteriological criteria required for the conservation of the finished products throughout their normal period of use, food-compatibility of the treatment method and of the elements liable to form a part of this treatment, treatment costs compatible with the value of the finished products, and industrializable treatment.

BRIEF DESCRIPTION OF THE DRAWINGS

FIG. 1 shows the effects of the amount of dextrose and lysozyme on the growth of a strain of *Staphylococcus aureus* over time. Sample 1=0% dextrose, 0 ppm lysozyme; sample 2=0% dextrose, 1000 ppm lysozyme; sample 3=24.2% dextrose, 500 ppm lysozyme; sample 4=41.7% dextrose, 0 ppm lysozyme; and sample 5=41.7% dextrose, 1000 ppm lysozyme.

FIG. 2 shows the ability of a food composition according to the invention to inhibit or reduce bacterial population levels when artificially contaminated with *E. coli* or *S. aureus*. Solid square=composition according to the invention contaminated with *E. coli*; solid diamond=composition according to the invention contaminated with *S. aureus*; open square=composition not according to the invention contaminated with *E. coli*; and open diamond=composition not according to the invention contaminated with *S. aureus*.

DETAILED DESCRIPTION OF PREFERRED EMBODIMENTS

The present invention relates, firstly, to an essentially non-dairy aqueous food composition which is of constant bacteriological quality over a suitable period, comprising, as a component for substantially inhibiting bacterial growth, an effective amount of at least one monosaccharide which allows the osmotic pressure of the medium to be increased, and at least one bactericidal enzyme.

The expression "essentially non-dairy" is understood to mean that the composition comprises no milk fat or protein. On the other hand, the food composition can optionally contain lactoserum.

The expression "constant bacteriological quality over a suitable period" is understood to refer in particular to the qualities already mentioned above. In particular, it refers to compositions according to the invention having their bacterial populations stabilized or even reduced during storage for several days at 4° C., 60° C. or 10° C.

The expression "effective amount" is understood to refer to an amount which is sufficient to satisfy the storage criteria mentioned above.

The invention also relates to a method for inhibiting bacterial growth or for substantially reducing the bacterial population in a food composition or, possibly, in a cosmetic composition. The method is characterized in that an effective amount of a monosaccharide which allows the osmotic pressure of the medium to be increased and at least one bactericidal enzyme are added to the composition.

The reason for this is that the Applicant has observed, unexpectedly, that the combination of the two means:

increasing the osmotic pressure, obtained by a monosaccharide, and presence of a bactericidal enzyme leads to compositions which can be stored according to the required criteria.

One means for evaluating the osmotic pressure of a composition consists in measuring the water activity.

The water activity of a product is a notion which is well known in the food sector; this measurement, often abbreviated as Aw, measures the availability of water in a sample. In most cases, this water activity is not proportional to the water content of the product.

For example, mention may be made of:

chocolate: about 1% water: Aw=0.50 glycerol at a concentration of 10% in water: Aw=0.95.

The methods for measuring the water activity of a product are known to those skilled in the art.

In the case of an essentially non-dairy aqueous food composition, the water activity, in the absence of the component which substantially inhibits bacterial growth, is about 0.99.

According to one aspect of the present invention, the food composition is characterized in that, before adding the component, it has a water activity of greater than 0.96, and in that the monosaccharide allows the water activity to be lowered to below 0.95, preferably below 0.94.

In general, the water activity of the resulting food composition will thus be between 0.90 and 0.95 or advantageously between 0.90 and 0.94.

According to another aspect of the present invention, the food composition comprises one or more foods liable to result in bacterial contamination of the food composition.

Among these foods, mention may be made of those chosen from the group consisting of chocolate, egg yolk, cereals, spices, biscuits, dried fruit, dehydrated fruit and powders based on these products. Under certain conditions, egg white can also prove to be slightly contaminating.

The food composition can also comprise various other agents such as thickeners, texturing agents or gelling agents. Among these, mention may be made of xanthan gum, starch or other equivalent agents.

The monosaccharides which allow the present invention to be carried out are preferably chosen from the group consisting of glucose, D-glucose or dextrose, and fructose.

Needless to say, the invention is not limited to the monosaccharides specifically mentioned, but, rather, covers other monosaccharides which would also allow the osmotic pressure, and more precisely the water activity, to be lowered, as mentioned above.

Advantageously, the food composition will comprise, in percentage by weight, from 6 to 25% of the monosaccharides, advantageously 10 to 20%.

The enzymes which are particularly suitable are chosen from these present in the white of eggs, in particular of hen's eggs, of which mention may be made of ovotransferrin or conalbumin, avidin and lysozyme.

It is known that these enzymes are present in egg white in amounts approximately of 12% for ovotransferrin, 3.5% for lysozyme and 0.05% for avidin.

A preferred food composition will comprise at least lysozyme. It is known that lysozyme dissolves the wall of certain bacteria by hydrolyzing the mucocomplex substance responsible for the rigid structure of the cell. This enzyme is more active on gram+ bacteria than on gram− bacteria.

Preferably, the food composition will comprise at least 100 ppm of lysozyme and advantageously between 300 and 3000 ppm. The upper limit is not crucial, since larger amounts may be used, although this does not provide any particular effect.

A preferred variant consists in using egg white, the bactericidal enzymes, in particular lysozyme, being contained in the egg white.

The invention is particularly advantageous for food compositions having a pH in the region of neutrality and generally between 5.5 and 9. Indeed, it will be recalled that food compositions with a pH of less than 4.5 are by nature bacteriostatic or even bactericidal.

Preferably, the pH of these compositions is between 6 and 7.

The food compositions according to the invention are advantageously characterized in that they are of constant bacteriological quality for at least 28 days at 10° C.

A second advantageous characteristic of these compositions is that they are of constant bacteriological quality for at least 6 hours at 30° C.

An important characteristic of some of the compositions according to the invention is that they are non-sterile compositions which, by the means described above, have no risk of bacteriological degradation over the required period.

A preferred variant according to the invention relates to a food composition which satisfies the bacteriological quality criteria mentioned above. It is in the form of fresh produce, in particular in mousse form, with a water activity of between 0.9 and 0.95, a pH of between 5.5 and 9, and it has the following composition in percentage by weight:

| | |
|---|---|
| food liable to result in bacterial contamination, such as chocolate | 20 to 40% |
| egg yolk | 5 to 15% |
| monosaccharide | 10 to 20% |
| egg white | 20 to 45% |
| water | 5 to 17% | and optionally starch, glucose syrup, a gum arabic and NaCl.

Preferably, this composition is characterized in that it has the following composition in percentage by weight:

| | |
|---|---|
| chocolate | 21 to 35% |
| egg yolk | 5 to 15% |
| dextrose | 10 to 20% |
| egg white | 25 to 40% |
| water | 5 to 17% | and optionally starch, glucose syrup, a gum arabic and NaCl.

This food composition can in particular be a dessert.

It has already been explained in the above description that the invention relates to a food composition containing a component which allows the osmotic pressure of the medium to be increased (which is measured experimentally by lowering the water activity) by means of a monosaccharide, in particular dextrose, and by the presence of a bactericidal enzyme.

The invention consequently also relates to a method for inhibiting bacterial growth or for substantially reducing the bacterial population in a food or cosmetic composition, characterized in that an effective amount of a monosaccharide which allows the osmotic pressure of the medium to be increased and at least one bactericidal enzyme as above are added to the said composition.

Although applicable mainly to food compositions, this method can also be applied to cosmetic compositions which require bacteriological stability.

The term cosmetic compositions is understood to refer to any composition which needs to be applied topically and externally.

The bacteria which this type of method concerns are many and varied and are, in particular, pathogenic bacteria, sporulated bacteria and contaminating bacteria.

Mention may be made, in a non-limiting manner, of the following bacteria:

*Staphylococcus hominis, Staphylococcus warnerie, Staphylococcus aureus, Listeria monocytogenes, Salmonella* typhimurium, Salmonella enteridis, 2 strains of Salmonella isolated from egg products, 2 strains of Salmonella isolated from cocoa beans, *Bacillus cereus, Bacillus subtilis, Bacillus pumilus*, micrococcus spp., *Enterococcus faecium, Enterobacter cloacae, Escherichia coli, Klebsiella pneumoniae*, Leuconostoc spp., *Pseudomonas aeruginosa, Flora Danica*.

These strains include the pathogenic bacteria occurring in the dairy sector and in egg products, as well as the bacteria most commonly occurring in the dairy, chocolate and egg-product sectors.

The examples below illustrate the present invention without, however, limiting it.

Example 1

1. Test composition

The following example was carried out on a chocolate mousse, which had not been heat-treated, having the following composition in percentage by weight:

| | |
|---|---|
| chocolate | 28% |
| egg yolk | 10% |
| glucose syrup | 1.9% |
| starch | 0.56% |
| NaCl | 0.056% |
| xanthan | 0.019% |
| egg white | 32.5% |
| (including about 800 ppm of lysozyme) | |
| dextrose | 15.9% |
| water qs | 100% |

The water activity of such a composition is 0.928 and the pH is 6.5.

The chocolate mousse is prepared according to the following method:
 a) Mixing and sterilization of the ingredients (starch, NaCl, xanthan, glucose syrup, dextrose, water)
 b) Injection of egg white
 c) Whipping
 d) Injection of egg yolk
 e) Injection of chocolate
 f) Mixing It will be noted that beyond step b), no heat treatment or standard removal of bacteria is applied.

2. Contamination tests

This mousse was artificially contaminated with various types of potentially pathogenic bacteria (*B. cereus, E. coli, S. aureus, S. enteritidis, L. monocyto-genes*). The change in this flora was studied at 1, 7, 14, 21 and 28 days of storage at 10° C. The results represented in the table below demonstrate an absence of growth of the *B. cereus* strain or even a significant reduction in the *E. coli, S. aureus, S. enteritidis* and *L. monocytogenes* strains.

| | CFU/g count after different days (D) of storage at 10° C. | | | | | |
|---|---|---|---|---|---|---|
| Bacteria | D0 | D1 | D7 | D14 | D21 | D28 |
| *B. cereus* | $8.5 \times 10^3$ | $3.0 \times 10^3$ | $4.0 \times 10^3$ | $4.0 \times 10^3$ | $1.0 \times 10^4$ | $2.2 \times 10^3$ |
| *E. coli* | $1.3 \times 10^6$ | $1.2 \times 10^6$ | $6.5 \times 10^5$ | $1.8 \times 10^5$ | $4.5 \times 10^4$ | $1.7 \times 10^4$ |
| *S. aureus* | $4.0 \times 10^6$ | $9.5 \times 10^5$ | $3.0 \times 10^4$ | $3.0 \times 10^3$ | $1.0 \times 10^2$ | 50 |
| *S. enteritidis* | $1.8 \times 10^4$ | $1.2 \times 10^4$ | $8 \times 10^3$ | $4.1 \times 10^3$ | $1.3 \times 10^3$ | $4.9 \times 10^2$ |
| *L. monocytogenes* | $1.8 \times 10^4$ | $9.3 \times 10^3$ | $1.3 \times 10^3$ | $3.3 \times 10^2$ | $1.4 \times 10^2$ | $1.3 \times 10^2$ |

After storage for 24 hours at 30° C., no microbial growth was observed in the chocolate mousse according to the results indicated below:

| | CFU/g count after 24 hours (24 h) of storage at 30° C. | |
|---|---|---|
| Bacteria | 0 h | 24 h |
| *B. cereus* | $1.3 \times 10^4$ | $6.5 \times 10^3$ |
| *E. coli* | $3.0 \times 10^4$ | $8.0 \times 10^3$ |
| *S. aureus* | $8.0 \times 10^4$ | $2.5 \times 10^3$ |

By means of an astute choice of the osmotic pressure and the antibacterial activity of components of the egg white, the bacteriological qualities of a chocolate mousse could be maintained, while at the same time conserving its organoleptic characteristics.

Example 2 in vitro test on the influence of the percentage of dextrose and of lysozyme (LYS in ppm) on the growth of a strain of *Staphylococcus aureus*.

The log (CFU/g) count was measured as a function of the storage time in days at 10° C. for 5 tests involving different concentrations of dextrose and of lysozyme.

| Test | Dex (%) | LYS (ppm)* |
|---|---|---|
| 1 | 0 | 0 |
| 2 | 0 | 1000 |
| 3 | 24.2 | 500 |
| 4 | 41.7 | 0 |
| 5 | 41.7 | 1000 |

The amount of lysozyme is determined by means of a concentration as lysozyme hydrochloride.

The results are given in FIG. 1 and demonstrate the advantageous effect of the component according to the invention.

Example 3 Comparative test

A chocolate mousse similar to that of Example 1 but containing the sugar composition below was tested under the same conditions as those of Example 1 after contamination with *E. coli* and *S. aureus*.

| Composition (Comparative) | |
|---|---|
| Egg white | 30% |
| Chocolate | 27% |
| Butter | 20% |
| Sucrose | 12% |
| Egg yolk | 8% |
| Powdered egg white | 3% |
| Aw = 0.93. | |

After the composition Examples 1 and 3 had been artificially contaminated with a strain of S. aureus and a strain of E. coli, the change in the flora was studied after 1, 7, 14, 21 and 28 days of storage at 10° C. The results given in the attached FIG. 2 demonstrate a significant reduction of the E. coli and S. aureus strains in the composition of Example 1, whereas, for the comparative composition, stability of the bacterial population is observed.

| | Explanation of the keys in FIG. 2 |
|---|---|
| ■ | composition 1 contaminated with E. coli (composition of |
| ♦ | composition 1 contaminated with S. aureus Example 1) |
| □ | composition 2 contaminated with E. coli (comparative |
| Δ | composition 2 contaminated with S. aureus composition) |

What is claimed is:

1. An essentially non-dairy aqueous food composition comprising 20 to 40% chocolate,
   wherein said food composition has a bacterial population and wherein said bacterial population does not increase for at least 28 days, and
   wherein said food composition comprises
      an amount of at least one monosaccharide sufficient to increase the osmotic pressure of the composition, and
      at least one bacteriocidal enzyme selected from the group consisting of ovotransferrin, conalbumin, avidin, and lysozyme,
   and wherein said food composition is not heated to keep its organoleptic nutritional, or technological value.

2. The food composition of claim 1, wherein said at least one monosaccharide is selected from the group consisting of glucose, D-glucose or dextrose, and fructose.

3. The food composition of claim 2, wherein said at least one monosaccharide is glucose.

4. The food composition of claim 2, wherein said at least one monosaccharide is D-glucose or dextrose.

5. The food composition of claim 2, wherein said at least one monosaccharide is fructose.

6. The food composition of claim 1, wherein inclusion of said at least one monosaccharide in the composition lowers the water activity of the composition from greater than 0.96 to lower than 0.95.

7. The food composition of claim 6, wherein said at least one monosaccharide is selected from the group consisting of glucose, D-glucose or dextrose, and fructose.

8. The food composition of claim 7, wherein said composition comprises 6 to 25% by weight of said at least one monosaccharide.

9. The food composition of claim 8, wherein said composition comprises 10 to 20% by weight of said at least one monosaccharide.

10. The food composition of claim 1, wherein the composition has a water activity of lower than 0.94.

11. The food composition of claim 1, wherein said composition comprises 6 to 25% by weight of said at least one monosaccharide.

12. The food composition of claim 11, wherein said composition comprises 10 to 20% by weight of said at least one monosaccharide.

13. The food composition of claim 1, wherein said composition comprises between 300 and 3000 ppm lysozyme.

14. The food composition of claim 13, wherein said composition comprises egg white, and wherein said lysozyme is present in the egg white.

15. The food composition of claim 1, wherein said composition comprises egg white, and wherein said at least one bacteriocidal enzyme is present in the egg white.

16. The food composition of claim 1, wherein the pH of the composition is between 5.5 and 9.

17. An essentially non-dairy aqueous food composition comprising 20 to 40% chocolate,
   wherein said food composition has a bacterial population and wherein said bacterial population does not increase for at least 28 days at 10° C., and
   wherein said food composition comprises
      an amount of at least one monosaccharide sufficient to increase the osmotic pressure of the composition, and
      at least one bacteriocidal enzyme selected from the group consisting of ovotransferrin, conalbumin, avidin, and lysozyme,
   and wherein said food composition is not heated to keep its organoleptic nutritional, or technological value.

18. The food composition of claim 17, wherein the composition is fresh produce with a water activity of between 0.9 and 0.95 and a pH of between 5.5 and 9, wherein said composition comprises the following components, in weight percentage:

| chocolate | 20 to 40% |
|---|---|
| egg yolk | 5 to 15% |
| monosaccharide | 10 to 20% |
| egg white | 20 to 45% |
| water | 5 to 17%. |

19. The food composition of claim 18, further comprising starch, glucose syrup, a gum arabic, NaCl, or any combination thereof.

20. The food composition of claim 18, which is a dessert.

21. The food composition of claim 18, wherein said composition comprises the following components, in weight percentage:

| chocolate | 23 to 35% |
|---|---|
| egg yolk | 5 to 15% |
| dextrose | 10 to 20% |
| egg white | 25 to 40% |
| water | 5 to 17%. |

22. The food composition of claim 21, further comprising starch, glucose syrup, a gum arabic, NaCl, or any combination thereof.

23. An essentially non-dairy aqueous food composition comprising 20 to 40% chocolate,
   wherein said food composition has a bacterial population and wherein said bacterial population does not increase for at least 6 hours at 30° C., and
   wherein said food composition comprises
      an amount of at least one monosaccharide sufficient to increase the osmotic pressure of the composition, and at least one bacteriocidal enzyme selected from the group consisting of ovotransferrin, conalbumin, avidin, and lysozyme, and wherein said food composition is not heated to keep its organoleptic, nutritional, or technological value.

24. The food composition of claim 23, wherein the composition is fresh produce with a water activity of between 0.9 and 0.95 and a pH of between 5.5 and 9, wherein said composition comprises the following components, in weight percentage:

| | |
|---|---|
| chocolate | 20 to 40% |
| egg yolk | 5 to 15% |
| monosaccharide | 10 to 20% |
| egg white | 20 to 45% |
| water | 5 to 17%. |

25. The food composition of claim 24, further comprising starch, glucose syrup, a gum arabic, NaCl, or any combination thereof.

26. The food composition of claim 24, which is a dessert.

27. The food composition of claim 24, wherein said composition comprises the following components, in weight percentage:

| | |
|---|---|
| chocolate | 23 to 35% |
| egg yolk | 5 to 15% |
| dextrose | 10 to 20% |
| egg white | 25 to 40% |
| water | 5 to 17%. |

28. The food composition of claim 27, further comprising starch, glucose syrup, a gum arabic, NaCl, or any combination thereof.

29. A method of inhibiting an increase in a bacterial population present in an essentially non-dairy aqueous chocolate food composition, said method comprising combining an essentially non-dairy aqueous chocolate food composition comprising 20–40% chocolate, by weight percent, with an amount of at least one monosaccharide sufficient to raise the osmotic pressure of the food composition, and at least one bacteriocidal enzyme selected from the group consisting of ovotransferrin, conalbumin, avidin, and lysozyme, without heating the food composition to prevent the loss of its organoleptic, nutritional, or technological value.

30. The method of claim 29, wherein said at least one monosaccharide is selected from the group consisting of glucose, D-glucose or dextrose, and fructose.

31. The method of claim 29, wherein said bacterial population comprises bacteria selected from the group consisting of pathogenic bacteria, sporulated bacteria, and contaminating bacteria.

* * * * *

UNITED STATES PATENT AND TRADEMARK OFFICE
CERTIFICATE OF CORRECTION

PATENT NO. : 6,099,883
DATED : August 8, 2000
INVENTOR(S) : Francois Colomban et al.

It is certified that error appears in the above-identified patent and that said Letters Patent is hereby corrected as shown below:

Title page,
Item [75], in the inventors, line 1, "Benoît" should read -- Benoît --.

Claim 27, column 9,
Line 24, "claim 24" should read -- claim 23 --.

Signed and Sealed this

Second Day of October, 2001

Attest:

*Nicholas P. Godici*

NICHOLAS P. GODICI
*Attesting Officer*        *Acting Director of the United States Patent and Trademark Office*